United States Patent [19]
Eckert et al.

[11] Patent Number: 5,423,795
[45] Date of Patent: Jun. 13, 1995

[54] RESECTOSCOPE

[75] Inventors: Rainer Eckert, Ludwigsburg; Manfred Dangelmaier, Weinstadt; Ralf Breining, Ostfildern; Johannes Solf, Sindelfingen; Ludwig Bonnet, Knittlingen, all of Germany

[73] Assignee: Richard Wolf GmbH, Knittlingen, Germany

[21] Appl. No.: 118,163

[22] Filed: Sep. 8, 1993

[30] Foreign Application Priority Data

Mar. 8, 1993 [DE] Germany ............... 9303240 U

[51] Int. Cl.⁶ ............................................. A61B 17/36
[52] U.S. Cl. ................................ 606/1; 606/45; 606/46; 128/4
[58] Field of Search ............. 128/4, 6; 606/46–49, 606/205–207

[56] References Cited
U.S. PATENT DOCUMENTS

| | | | |
|---|---|---|---|
| 3,895,636 | 7/1975 | Schmidt | 606/205 |
| 3,903,892 | 9/1975 | Komiya | 606/46 |
| 4,430,996 | 2/1984 | Bonnet | |
| 5,217,458 | 6/1993 | Parins | 606/48 |

*Primary Examiner*—Stephen C. Pellegrino
*Assistant Examiner*—Michael Peffley
*Attorney, Agent, or Firm*—Panitch Schwarze Jacobs & Nadel

[57] ABSTRACT

A resectoscope has a shaft and a lock body which is slidable along the shaft and to which the proximal end portion of a resection electrode can be fixed. A handle is provided for displacing the lock body and thus the electrode along the shaft. The handle consists of a first portion connected to the lock body and projecting radially outwardly of the lock body and a second portion connected to the shaft, for engagement by a thumb of the user of the resectoscope. The first portion of the handle is formed as a disc provided with gripping aids for the user's fingers.

8 Claims, 2 Drawing Sheets

RESECTOSCOPE

FIELD OF THE INVENTION

This invention relates to a resectoscope comprising a shaft, and a lock body displaceable on the shaft, for fixedly receiving the proximal end portion of a high frequency resection electrode, the lock body and thus the electrode being displaceable relative to the shaft by operation of a handle. The handle consists of a first portion connected to the lock body and projecting radially outwardly thereof and a second portion connected to the shaft, for engagement by a thumb of the user of the resectoscope.

BACKGROUND OF THE INVENTION

According to German Utility Model No 7924 359 U.S. Pat. No. 4,430,996 the first handle portion of such a resectoscope is in the form of a grip and the second handle portion thereof is in the form of a ring for receiving the user's thumb while the other fingers of the same hand encompass or extend through the grip. In some resectoscopes a handle portion for use in turning the high frequency cutting element of the resectoscope is in the form of an adjusting wheel the circumference of which has rounded recesses providing gripping surfaces.

During a resection operation the lock body of the resectoscope together with the electrode, the shaft and an outer shaft fitted thereover may need to be rotated by as much as 360° about the longitudinal axis of the resectoscope. The use of resectoscopes having conventional handles may, therefore, be undesirably laborious since the shape and arrangement of such handles is not ergonomically optimal, so that the user must frequently regrip such a handle and at the same time change the position of his arm, during a resection operation.

SUMMARY OF THE INVENTION

An object of the invention is an improved resectoscope having a handle which is of optimal design and operation.

To this end the first handle portion of the resectoscope is a disc provided with finger gripping aids. The finger gripping aids are preferably apertures, especially circular holes in the disc arranged in a circle around the longitudinal axis of the shaft. The user can rotate the resectoscope by engaging at least one finger with a finger gripping aid of the disc to apply pushing or pulling pressure to the disc, with the thumb of the same hand engaging the second portion of the handle.

The second handle portion is preferably a thumb ring having a thumb rest surface and is preferably rotatably mounted to the resectoscope (i.e., to the shaft thereof) so that the position of the thumb and thus also the position of the user's hand and arm do not need to be altered when the remainder of the resectoscope is being rotated, since the position of the second handle portion, which is determined by the thumb, does not need to be altered.

The disc preferably has a circular periphery and is preferably concave as seen from the proximal end of the resectoscope. Such configuration of the disc facilitates rotation of the resectoscope since those fingers which do not engage a finger gripping aid can rest naturally and comfortably against the distal surface of the disc.

DETAILED DESCRIPTION OF THE PREFERRED EMBODIMENT OF THE INVENTION

Figure 1:
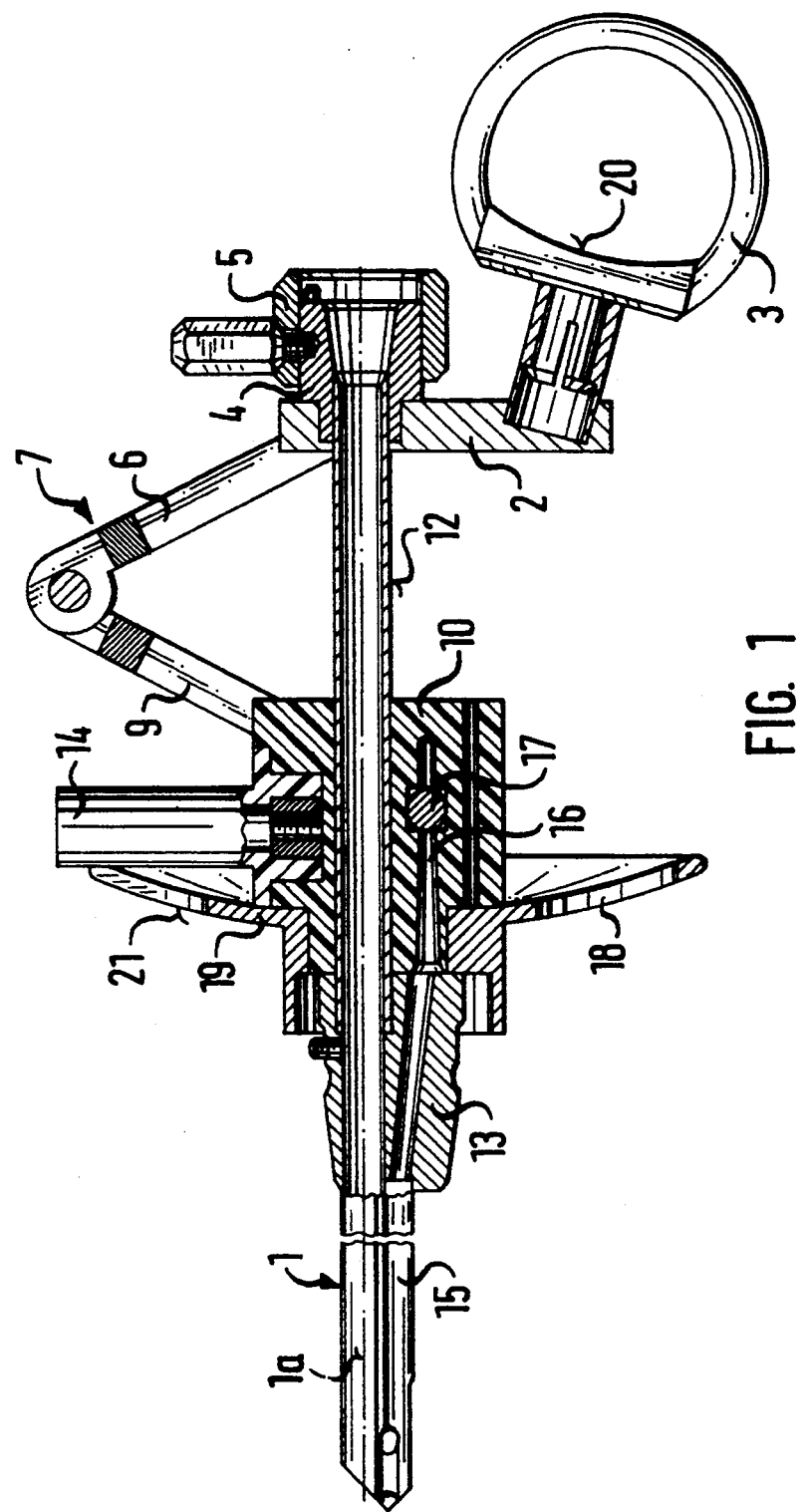
FIG. 1 is a longitudinal sectional view through a resectoscope according to the preferred embodiment of the invention.

The resectoscope comprises a shaft 1 having at the proximal end thereof a connecting strap 2 extending perpendicularly to the longitudinal axis 1a of the shaft 1. A thumb ring 3, constituting the second handle portion of the resectoscope, is connected to the lower end of the strap 2. A frusto-conical receptacle 4 having a clamping ring 5 for receiving a lens and locking the lens therein is connected to the upper end of the strap 2. One arm 6 of a two armed hinged bridge 7 is also pivotally attached to the upper end of the connecting strap 2, the other arm 9 of the bridge 7 being pivotally attached to a plastic, high frequency electrode lock body 10 which is slidable along a proximal length 12 of the shaft 1. A torsion spring 11 acting between the arms 7 and 9 urges the lock body 10 distally of the shaft 1 and towards a frusto-conical coupling member 13 fixed to the shaft 1, for coupling an outer shaft (not shown) to the resectoscope. In its distal end position the lock body 10 abuts against the proximal end wall of the coupling member 13 as shown in FIG. 1. A channel 15 in the shaft 1 through which a high frequency resection electrode (not shown) can be inserted communicates with a bore 13' extending through the coupling member 13.

Figure 2:
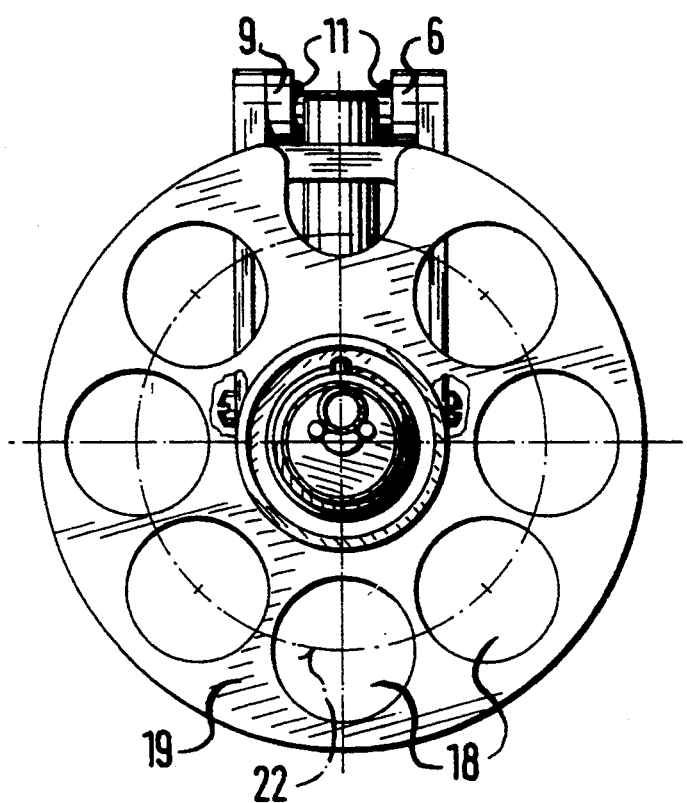
FIG. 2 is an end view of the resectoscope of FIG. 1.

The lock body 10 has an axial bore 16 for receiving said electrode. A compression spring biased, electrode locking element 17, electrically connected by means of a lead (not shown) to a high frequency terminal 14 on top of the body 10, extends through the body 10, perpendicularly with respect to the bore 16. The locking element 17 has a transverse, through bore (not shown) approximately aligned with the bore 16. In order to assemble the resection electrode to the resectoscope, the proximal end of the resection electrode is introduced, in the proximal direction of the resectoscope, through the channel 15, the bore 13' in the element 13, and the bore 16, so that the proximal end of the electrode passes through the bore in the locking element 17 against the action of its compression spring, up to the proximal end of the bore 16, whereafter the locking element 17 is urged by its compression spring against the electrode to clamp in to the lock body 10. High frequency current is supplied to the resectioning electrode by way of the terminal 14, the lead and the locking element 17. A disc 19 having a circular periphery and constituting the first handle portion of the resectoscope, is fixed to the distal end face of the lock body 10. According to the present example, and as shown in FIG. 2, the disc 19 is formed with a ring of circular holes 18 the centres of which lie upon an imaginary circle 22 around the longitudinal axis 1a of the shaft 1. The disc 19 is curved, as seen in section in FIG. 1, so as to be concave towards the proximal end of the resectoscope, the distal surface 21 of the disc 19 being convex. The ring 3 is provided with a thumb rest 20 and is rotatably secured to the strap 2.

For the performance of a resection the high frequency electrode is assembled to the resectoscope as described above, said outer shaft is assembled over the distal end portion of the shaft 21 and is locked to the coupling member 13, and the outer shaft is inserted into a bodily duct, for example the urethra, to be treated. During resection, the thumb of the user's hand is passed through the thumb ring 3 and rests on the thumb rest 20, the remaining fingers of the user's hand being applied to the distal surface 21 of the disc 19. The user thereby applies proximally directed pressure to the disc 19 to displace the disc 19, together with the lock body 10 and the high frequency electrode in the proximal direction so that the distal end of the electrode, which is, for example, in the form of a cutting loop, is moved to pare down tissue. The electrode is moved in the return direction under the action of the spring 11 as soon as the user relieves the pressure on the disc 19, since the spring 11 urges the arms 6 and 9 of the bridge 7 relatively apart so that the arm 9 displaces the lock body 10 and thus the electrode which is clamped thereto, in the distal direction. The user can readily rotate the resectoscope by gripping the disc 19 with the index finger, for example, above the rest and with the ring finger below the rest, in one of the holes 18 located in the region of the terminal 14, and rotating the resectoscope by pulling or pressing with one of these two fingers. The thumb and the hand can remain in their initial positions, since as mentioned above the thumb ring 3 is rotatably secured to the strap 2. By virtue of the proximal concavity of the disc 19, those fingers which are not inserted through holes 18 can rest naturally against the distal surface 21 of the disc 19 so that rotation of the resectoscope is facilitated.

The disc 19 may, in addition to, or instead of, the holes 18, be formed with other finger gripping aids, for example, in the form of projections and depressions in the vicinity of the outer periphery of the disc 19. The other finger gripping aids may be in the form of radial recesses in the periphery of the disc 19 one of which is shown at the top thereof in FIGS. 1 and 2.

What is claimed is:

1. A resectoscope, comprising:
   a shaft;
   a lock body displaceable on the shaft, said lock body having means for fixedly receiving the proximal end portion of a high frequency resection electrode for displacement relative to the shaft; and
   a handle for displacing the lock body and thus the electrode, relative to the shaft, the handle comprising a first handle portion connected to the lock body and projecting radially outwardly thereof and a second handle portion connected to the shaft, for engagement by a thumb of a user of the resectoscope, the first handle portion being a disc provided with aids for gripping with fingers of the user, said aids comprising circular holes in said disc and being arranged in a circle about a longitudinal axis of the shaft.

2. A resectoscope as claimed in claim 1, wherein the disc has a circular circumferential edge and is concave in the proximal direction of the shaft.

3. A resectoscope as claimed in claim 1, wherein the second handle portion is rotatably secured to the shaft.

4. A resectoscope as claimed in claim 3, wherein the second handle portion is a thumb ring having a thumb rest.

5. A resectoscope, comprising:
   a shaft;
   a lock body displaceable on the shaft, said lock body having means for fixedly receiving the proximal end portion of a high frequency resection electrode for displacement relative to the shaft; and
   a handle for displacing the lock body and thus the electrode, relative to the shaft, the handle comprising a first handle portion connected to the lock body and projecting radially outwardly thereof and a second handle portion connected to the shaft, for engagement by a thumb of a user of the resectoscope, the first handle portion being a disc provided with aids for gripping with fingers of the user, said aids comprising circular holes in said disc, and said disc having a circular circumferential edge and being concave in the proximal direction of the shaft.

6. A resectoscope as claimed in claim 5, wherein said aids are arranged in a circle about a longitudinal axis of the shaft.

7. A resectoscope as claimed in claim 5, wherein the second handle portion is rotatably secured to the shaft.

cm 8. A resectoscope as claimed in claim 7, wherein the second handle portion is a thumb ring having a thumb rest.

8. A resectoscope as claimed in claim 7, wherein the second handle portion is a thumb ring having a thumb rest.

* * * * *